United States Patent
Shih et al.

(10) Patent No.: US 11,246,822 B2
(45) Date of Patent: Feb. 15, 2022

(54) BIOMEDICAL COMPOSITION FOR SKIN CARE AND/OR MAINTENANCE AND DELAYING AND/OR INHIBITING SKIN AGING AND THE USE THEREOF

(71) Applicant: INDUSTRIAL TECHNOLOGY RESEARCH INSTITUTE, Hsinchu (TW)

(72) Inventors: Ting-Yu Shih, Taipei (TW); Lu-Chih Wang, New Taipei (TW); Yuan-Kun Yu, Yilan (TW); Yi-Ting Hsieh, Zhudong Township (TW); Yu-Chun Liu, Taichung (TW); Jing-Wen Tang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 98 days.

(21) Appl. No.: 16/730,564

(22) Filed: Dec. 30, 2019

(65) Prior Publication Data
US 2020/0375873 A1  Dec. 3, 2020

(30) Foreign Application Priority Data

May 30, 2019 (TW) ................... 108118735

(51) Int. Cl.
*A61K 8/00* (2006.01)
*A61K 8/73* (2006.01)
(Continued)

(52) U.S. Cl.
CPC ............ *A61K 8/735* (2013.01); *A61K 8/0291* (2013.01); *A61K 8/04* (2013.01); *A61K 8/06* (2013.01);
(Continued)

(58) Field of Classification Search
CPC ..................................... A61K 8/735
See application file for complete search history.

(56) References Cited

U.S. PATENT DOCUMENTS

| 6,440,433 B1 | 8/2002 | Breton et al. |
| 8,940,333 B2 | 1/2015 | Hsieh et al. |
| | (Continued) | |

FOREIGN PATENT DOCUMENTS

| CN | 104548109 A | 4/2015 |
| CN | 105085708 A | 11/2015 |
| | (Continued) | |

OTHER PUBLICATIONS

Prikhnenko (Clin Cosmet Investig Dermatol. 2015; 8: 151-157). (Year: 2015).*

(Continued)

*Primary Examiner* — Benjamin J Packard
(74) *Attorney, Agent, or Firm* — Birch, Stewart, Kolasch & Birch, LLP

(57) ABSTRACT

A method for skin care and/or maintenance including applying or administering a preparation to a subject is provided. The preparation includes a biomedical composition, and the biomedical composition includes an effective amount of micelle, wherein the micelle includes a hyaluronic acid and/or a derivative thereof and a modified histidine. The modified histidine is grafted to at least one primary hydroxyl group of the hyaluronic acid and/or the derivative thereof, and a graft ratio of the modified histidine is 1-100%. Moreover, the hyaluronic acid and/or the derivative thereof and the modified histidine form the micelle on a weight percentage of 0.2-300:1.

17 Claims, 8 Drawing Sheets

(51) Int. Cl.
| | |
|---|---|
| A61K 8/06 | (2006.01) |
| A61K 8/49 | (2006.01) |
| A61Q 19/08 | (2006.01) |
| A61K 8/04 | (2006.01) |
| A61K 9/107 | (2006.01) |
| A61K 31/728 | (2006.01) |
| A61K 9/00 | (2006.01) |
| A61K 31/4172 | (2006.01) |
| A61K 31/375 | (2006.01) |
| A61K 8/67 | (2006.01) |
| A61K 31/015 | (2006.01) |
| A61K 8/02 | (2006.01) |
| A61K 8/96 | (2006.01) |

(52) U.S. Cl.
CPC .............. *A61K 8/494* (2013.01); *A61K 8/671* (2013.01); *A61K 8/676* (2013.01); *A61K 8/96* (2013.01); *A61K 9/0014* (2013.01); *A61K 9/1075* (2013.01); *A61K 31/015* (2013.01); *A61K 31/375* (2013.01); *A61K 31/4172* (2013.01); *A61K 31/728* (2013.01); *A61Q 19/08* (2013.01)

(56) References Cited

U.S. PATENT DOCUMENTS

| | | | |
|---|---|---|---|
| 8,999,300 | B2 | 4/2015 | Iwama et al. |
| 9,072,919 | B2 | 7/2015 | Pan et al. |
| 9,725,483 | B2 | 8/2017 | García Antón et al. |
| 2004/0265268 | A1 | 12/2004 | Jain |
| 2015/0118322 | A1* | 4/2015 | Lo ..................... A61K 31/4172 424/649 |
| 2016/0113905 | A1 | 4/2016 | Shih et al. |

FOREIGN PATENT DOCUMENTS

| | | |
|---|---|---|
| CN | 109806182 A | 5/2019 |
| TW | 201515661 A | 5/2015 |
| TW | I603731 B | 11/2017 |

OTHER PUBLICATIONS

Chen el al., The Research Progress in Hyaluronic Acid,* China Biotechnology, vol. 35, No. 2, Feb. 17, 2015, pp. 111-118.

Taiwanese Office Action and Search Report, dated Jul. 14, 2020, for Taiwanese Application No. 108118735.

Jiang et al., "Technology of Biotech Fermentation Industry," China Light Industry Press, May 31, 2016, pp. 345-355 with English abstract (4 pages total).

Waring, "Eat Beautiful," Nov. 30, 2018, p. 27 with English abstract (3 pages total).

Zhang et al., "Clinical efficiency of antimicrobial peptide and hyaluronic acid in the treatment of moderate—serious acne vulgaris," Journal of Clinical and Experimental Medicine, vol. 16, No. 13, Jul. 2017, pp. 1351-1353, with English abstract.

* cited by examiner

BIOMEDICAL COMPOSITION FOR SKIN CARE AND/OR MAINTENANCE AND DELAYING AND/OR INHIBITING SKIN AGING AND THE USE THEREOF

CROSS REFERENCE TO RELATED APPLICATION

The present application is based on, and claims priority from, Taiwan Application Ser. No. 108118735, filed on May 30, 2019, the disclosure of which is hereby incorporated by reference herein in its entirety.

TECHNICAL FIELD

The present disclosure relates to a biomedical composition for skin care and/or maintenance, and for delaying and/or inhibiting skin aging, and the use thereof.

BACKGROUND

How to maintain youth and fight against aging and wrinkles of the skin is a topic that many modern people focus on—both men and women. According to the report provided by Mintel Group Ltd., United Kingdom, air pollution and environmental stimuli will accelerate the aging of skin. Among those surveyed, 30% of people aged 20 to 49 said that they have problem with wrinkles, and nearly 40% of them are using anti-aging products at 20 to 24 years old. It is obvious that the demand for products in the anti-aging market is still increasing.

Hyaluronic acid (HA) is a polymer of disaccharides composed of D-glucuronic acid and N-acetyl D-glucosamine. In the hyaluronic acid, D-glucuronic acid and D-N-acetylglucosamine are linked via β-1,3 glycosidic bond while disaccharide units are linked to each other via β-1,4 glycosidic bonds. Generally, molecular weights of hyaluronic acid range from 5,000 to 20,000,000 Dalton (Da).

Studies have shown that hyaluronic acid plays a variety of important physiological functions in the living body, such as lubricating joints, regulating the permeability of blood vessel walls, regulating proteins, enhancing immunity, and promoting wound healing. At the same time, in medicine, hyaluronic acid can be used as an Auxiliary drug for arthritis treatment, ophthalmology, heart surgery, etc., and has a unique effect on treating scald, burns, frostbite and on artificial skin and the like.

However, with the increase of age and the influence of nutrition, sunshine and other factors, the ability of body to synthesize hyaluronic acid will gradually decline, and the hyaluronic acid content in the skin will gradually decrease. During the embryonic period, the human body has the highest content of hyaluronic acid, and after birth, it begins to decrease year by year. When the hyaluronic acid content in the skin is below a certain level, the water content of the skin surface layer will gradually decrease to cause the stratum corneum to age, and thus the skin appears rough and wrinkled and loses elasticity, and appears to be aging.

Therefore, the development of a skin care product which can stabilize the skin condition and activate the physiological function of the skin, and then activate the all-round anti-aging protection mechanism has been the subject of research and development for manufacturers in related fields.

BRIEF DESCRIPTION OF DRAWINGS

The present invention can be more fully understood by reading the subsequent detailed description and examples with references made to the accompanying drawings, wherein.

SUMMARY

Figure 1:
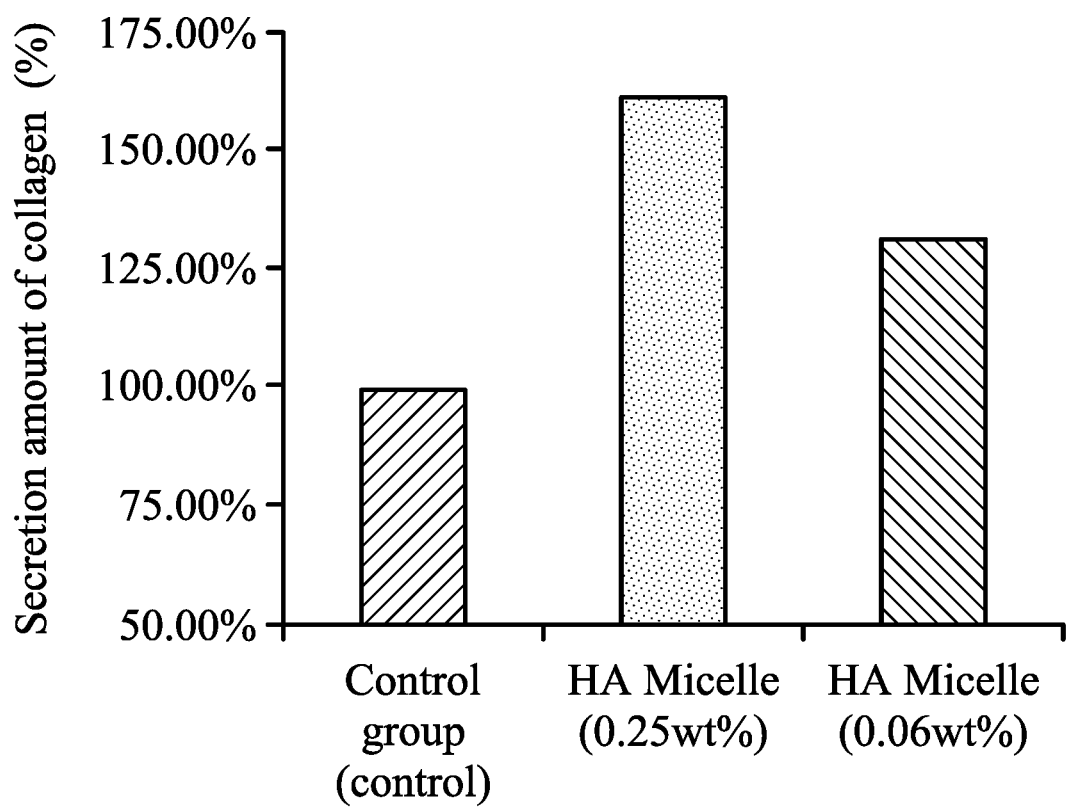
FIG. 1 shows the effect of HA micelle on collagen proliferation of human skin fibroblasts.

The present disclosure provides a method for skin care and/or maintenance, comprising applying or administering a preparation to a subject, wherein the preparation comprises a biomedical composition, and wherein the biomedical composition comprises an effective amount of micelle. The micelle comprises a hyaluronic acid and/or a derivative thereof and a modified histidine. The modified histidine is grafted to at least one primary hydroxyl group of the hyaluronic acid and/or the derivative thereof, and a graft ratio of the modified histidine is 1-100%. Moreover, the hyaluronic acid and/or the derivative thereof and the modified histidine form the micelle on a weight percentage of 0.2-300:1.

The present disclosure also provides a method for promoting collagen proliferation, growth factor secretion, and/or cytokine secretion, comprising applying or administering a preparation to a subject, wherein the preparation comprises a biomedical composition, and wherein the biomedical composition comprises an effective amount of micelle. The micelle comprises a hyaluronic acid and/or a derivative thereof and a modified histidine. The modified histidine is grafted to at least one primary hydroxyl group of the hyaluronic acid and/or the derivative thereof, and a graft ratio of the modified histidine is 1-100%. Moreover, the hyaluronic acid and/or the derivative thereof and the modified histidine form the micelle on a weight percentage of 0.2-300:1.

The present disclosure also provides a method for delaying and/or inhibiting skin aging, comprising applying or administering a preparation to a subject, wherein the preparation comprises a biomedical composition, and wherein the biomedical composition comprises an effective amount of micelle. The micelle comprises a hyaluronic acid and/or a derivative thereof and a modified histidine. The modified histidine is grafted to at least one primary hydroxyl group of the hyaluronic acid and/or the derivative thereof, and a graft ratio of the modified histidine is 1-100%. Moreover, the hyaluronic acid and/or the derivative thereof and the modified histidine form the micelle on a weight percentage of 0.2-300:1. Furthermore, the biomedical composition is further used in combination with at least one antioxidant, and the biomedical composition coats the at least one antioxidant in the form of the micelle.

The present disclosure further provides a biomedical composition. The biomedical composition comprises a hyaluronic acid and/or a derivative thereof, a modified histidine and at least one antioxidant. The modified histidine is grafted to at least one primary hydroxyl group of the hyaluronic acid and/or the derivative thereof, and the graft ratio of the modified histidine is 1-100%. Moreover, the hyaluronic acid and/or the derivative thereof and the modified histidine form an effective amount of micelle on a weight percentage of 0.2-300:1, and the weight ratio of the effective amount of micelle to the at least one antioxidant is 0.5-500.

A detailed description is given in the following embodiments with reference to the accompanying drawings.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure provides a biomedical composition, which can be used in the manufacture of a preparation for skin care and/or maintenance. Accordingly, the present disclosure also provides a method for skin care and/or maintenance, and the method for skin care and/or maintenance may comprise, but is not limited to applying or administering a preparation for skin care and/or maintenance to a subject, wherein the preparation comprises a biomedical composition.

The biomedical composition mentioned above may comprise, but is not limited to, an effective amount of micelle, and the micelle further may comprise a hyaluronic acid and/or a derivative thereof and a modified histidine. The modified histidine mentioned above is grafted to at least one primary hydroxyl group of the hyaluronic acid and/or the derivative thereof, and the graft ratio is 1-100%. Moreover, the foregoing hyaluronic acid and/or the derivative thereof and the modified histidine form the foregoing micelle on a weight percentage of 0.2-300:1.

In the biomedical composition, which can be used in the manufacture of a preparation for skin care and/or maintenance of the present disclosure, the at least one primary hydroxyl group of the hyaluronic acid mentioned above to which the modified histidine grafted may comprise a hydroxyl group located on the fifth carbon atom of a N-acetyl-D-glucosamine of at least one disaccharide unit of the hyaluronic acid, but it is not limited thereto.

In the biomedical composition, which can be used in the manufacture of a preparation for skin care and/or maintenance of the present disclosure, examples of suitable hyaluronic acid derivatives may comprise modification of hyaluronic acid by a cross-linking technique or a non-crosslinking technique. The crosslinking technique may comprise cross-linking hyaluronic acid with a crosslinker, for example, crosslinking a hyaluronic acid with adipic acid dihydrazide (ADH), crosslinking a hyaluronic acid with 1,4-butanediol diglycidyl ether (BDDE), crosslinking a hyaluronic acid with 1-ethyl-3-(3-dimethylaminopropyl) carbodiimide (EDC), crosslinking a hyaluronic acid with divinyl sulphone (DVS) crosslinking a hyaluronic acid with glycidyl methacrylate (GMA), modifying a hyaluronic acid with polylactic acid (PLA), modifying a hyaluronic acid with 4-vinylbenzyl chloride (VBC) and modifying a hyaluronic acid with cetyltrimethylammonium bromide (CTAB), or any combination thereof, but they are not limited thereto.

The non-crosslinking modification comprises grafting hyaluronic acid with a polylactic acid (PLA) to obtain a graft copolymer HA-PLA, and esterifying hyaluronic acid with 4-vinylbenzyl chloride (VBC) to obtain ester compound HA-VB, and hydrophobically modifying hyaluronic acid with cetyltrimethylammonium bromide (CTAB) to obtain hydrophobic cetyltrimethylammonium hyaluronate (CTA-HA), and then grafting hydrazine chloro-terminated lactic acid oligomer (OLA) (COL-OLA) onto CTA-HA to obtain CTA-HAOLA, or any combination of the foregoing, but is not limited thereto.

In the biomedical composition, which can be used in the manufacture of a preparation for skin care and/or maintenance of the present disclosure, the graft ratio of the modified histidine to hyaluronic acid and/or its derivative may be 1-100%. In one embodiment, the graft ratio of the modified histidine to hyaluronic acid and/or its derivative may be 1-80%. In another embodiment, the graft ratio of the modified histidine to hyaluronic acid and/or its derivative may be 1-60%. In another embodiment, the graft ratio of the modified histidine to hyaluronic acid and/or a derivative thereof may be 1-40%, but it is not limited thereto.

In the biomedical composition, which can be used in the manufacture of a preparation for skin care and/or maintenance of the present disclosure, which was mentioned above, a molecular weight of the hyaluronic acid or a derivative thereof may be about 7,000 to 1,500,000. In one embodiment, a molecular weight of the hyaluronic acid or a derivative thereof may be about 7,000 to 1,200,000. In another embodiment, a molecular weight of the hyaluronic acid or a derivative thereof may be about 7,000 to 800,000. In another embodiment, a molecular weight of the hyaluronic acid or a derivative thereof may be about 7,000-500,000. In another embodiment, a molecular weight of the hyaluronic acid or a derivative thereof may be about 7,000-350,000, but it is not limited thereto.

In the biomedical composition, which can be used in the manufacture of a preparation for skin care and/or maintenance of the present disclosure, which was mentioned above, examples of suitable modified histidines may comprise, for example, Boc-histidine, Cbz-histidine, Fmoc-histidine and Ac-histidine or the like, but it is not limited thereto.

In the biomedical composition, which can be used in the manufacture of a preparation for skin care and/or maintenance of the present disclosure, which was mentioned above, the hyaluronic acid and/or the derivative thereof and the modified histidine may form the micelle on a weight percentage of 0.2-300:1. In one embodiment, the hyaluronic acid and/or the derivative thereof and the modified histidine may form the micelle on a weight percentage of about 0.2-0.5:1, 0.3-0.7:1, 0.5-0.8:1, 0.75-5:1, 1-10:1, 5-20:1, 10-50:1, 30-100:1, 50-150:1, 80-180:1, 100-200:1, 150-250:1, 180-280:1, 100-300:1, but it not limited thereto. In another embodiment, the hyaluronic acid and/or the derivative thereof and the modified histidine may form the micelle on a weight percentage of about 0.2-200:1, 1-150:1, 5-100:1, but it is not limited thereto. In another embodiment, the hyaluronic acid and/or the derivative thereof and the modified histidine may form the micelle on a weight percentage of about 0.5:1, 5:1, 50:1, 100:1, 150:1, 200:1, 300:1, but it is not limited thereto.

In the biomedical composition, which can be used in the manufacture of a preparation for skin care and/or maintenance of the present disclosure, which was mentioned above, the particle size of the micelles formed from hyaluronic acid and/or its derivatives and modified histidine may be about 50-2000 nm. In one embodiment, the particle size of the above-mentioned micelles may be about 50-100 nm, 100-300 nm, 300-500 nm, 500-700 nm, 700-1000 nm, 1000-1500 nm, 1500-2000 nm, but it is not limited thereto. In another embodiment, the particle size of the above-mentioned micelles may be about 80-1800 nm, 100-1500 nm, 200-1200 nm, 300-1000 nm, 500-800 nm, but is not limited thereto. In another embodiment, the particle size of the above-mentioned micelles may be about 100 nm, 300 nm, 500 nm, 800 nm, 1000 nm, 1200 nm, 1500 nm, 1800 nm, but is not limited thereto.

In the biomedical composition, which can be used in the manufacture of a preparation for skin care and/or maintenance of the present disclosure, which was mentioned above, the preparation may be, but not limited to aqueous phase or oil phase. Moreover, the preparation may be, but not limited to an emulsion or a dispersion. Furthermore, the above biomedical composition may comprise, but is not limited to, an effective amount of micelle which is an active ingredient for skin care and/or maintenance, and percentage by weight of which is 0.001 wt %-1 wt %. In one embodiment, percentage by weight of the effective amount of micelle is 0.005 wt %-0.5 wt %. In another embodiment, percentage by weight of the effective amount of the micelle is 0.01 wt %-0.1 wt %, but it is not limited thereto.

In one embodiment, the biomedical composition can be used in the manufacture of a preparation for skin care and/or maintenance of the present disclosure, which was mentioned above may further comprise a pharmaceutically acceptable carrier or salt. The pharmaceutically acceptable carrier may comprise, but is not limited to, a solvent, a dispersion medium, a coating, an antibacterial and antifungal agent, or an isotonic and absorption delaying agent, etc. which is suitable for pharmaceutical administration. The biomedical composition mentioned above can be formulated into dosage forms for different administration routes utilizing conventional methods.

Furthermore, the pharmaceutically acceptable salt mentioned above may include, but is not limited to, salts including inorganic cation, such as alkali metal salts such as sodium salt, potassium salt or amine salt, such as alkaline-earth metal salt such as magnesium salt or calcium salt, such as the salt containing bivalent or quadrivalent cation such as zinc salt, aluminum salt or zirconium salt. In addition, the pharmaceutically acceptable salt may also be organic salt, such as dicyclohexylamine salt, methyl-D-glucamine, and amino acid salt such as arginine, lysine, histidine, or glutamine.

Moreover, the biomedical composition of the present disclosure may be administered orally, parenterally by an inhalation spray, or via an implanted reservoir to a subject. The parenteral methods may comprise applying the preparation by smearing it on skin, applying dressing on a wound or target region, subcutaneous, intracutaneous, intravenous, intramuscular, intra-articular, intra-arterial, intrasynovial, intrasternal, intrathecal, and intraleaional injection, as well as infusion techniques, but it is not limited thereto.

An oral composition may include, but is not limited to, tablets, capsules, emulsions, and aqueous suspensions, dispersions and solutions.

Similarly, a method for applying or administering the preparation for skin care and/or maintenance in the method for skin care and/or maintenance of the present disclosure mentioned above may be oral, parenteral by an inhalation spray, or via an implanted reservoir to a subject. The oral compositions and parenteral methods for applying or administering the preparation for skin care and/or maintenance may be the same as those for the biomedical composition which can be used in the manufacture of a preparation for skin care and/or maintenance mentioned above and will not be described again herein.

Furthermore, the subject in the method for skin care and/or maintenance of the present disclosure mentioned above may include, but is not limited to, a vertebrate. The vertebrate mentioned above may include a fish, an amphibian, a reptile, a bird, or a mammal, but it is not limited thereto. Examples of mammals include, but are not limited to, a human, an orangutan, a monkey, a horse, a donkey, a dog, a cat, a rabbit, a guinea pig, a rat, and a mouse. In one embodiment, the subject is a human.

The present disclosure further provides a biomedical composition that can be used in the manufacture of a preparation for promoting collagen proliferation, growth factor secretion, and/or cytokine secretion. Accordingly, the present disclosure also provides a method for promoting collagen proliferation, growth factor secretion, and/or cytokine secretion, and the method for skin care and/or maintenance may comprise, but is not limited to applying or administering a preparation for promoting collagen proliferation, growth factor secretion, and/or cytokine secretion to a subject, wherein the preparation comprises a biomedical composition.

The biomedical composition mentioned above may comprise, but is not limited to, an effective amount of micelle, and furthermore, the micelle may comprise a hyaluronic acid and/or a derivative thereof and a modified histidine. The modified histidine mentioned above is grafted to at least one primary hydroxyl group of the hyaluronic acid and/or the derivative thereof, and the graft ratio is 1-100%. Moreover, the foregoing hyaluronic acid and/or the derivative thereof and the modified histidine form the foregoing micelle on a weight percentage of 0.2-300:1.

In the above-mentioned biomedical composition of the present disclosure which can be used in the manufacture of a preparation for promoting collagen proliferation, growth factor secretion, and/or cytokine secretion, the growth factor and/or cytokine may comprise, but is not limited to, PDGF, FGF, GM-CSF, IL-1 or IL-8.

Moreover, in the biomedical composition, which can be used in the manufacture of a preparation for promoting collagen proliferation, growth factor secretion, and/or cytokine secretion of the present disclosure mentioned above, examples of suitable hyaluronic acid derivatives, grafting ratio of modified histidine to hyaluronic acid and/or its derivatives, molecular weight of hyaluronic acid and/or its derivatives, examples of suitable modified histidine and the like are further disclosed in the above description, and will not be described again herein.

Furthermore, in the biomedical composition, which can be used in the manufacture of a preparation for promoting collagen proliferation, growth factor secretion, and/or cytokine secretion of the present disclosure mentioned above, the percentage by weight of both of hyaluronic acid and/or a derivative thereof and the modified histidine for forming the micelle, a particle size of micelle formed by hyaluronic acid and/or a derivative thereof and modified histidine, the percentage by weight of an effective amount of micelle to the overall biomedical composition and the like are further disclosed in the above description, and will not be described again herein.

Furthermore, in the above-mentioned biomedical composition of the present disclosure which can be used in the manufacture of a preparation for promoting collagen proliferation, growth factor secretion, and/or cytokine secretion, the types of pharmaceutically acceptable carriers or salts, and an applying/administration technique for the biomedical composition can be the same as those for those for the biomedical composition which can be used in the manufacture of a preparation for skin care and/or maintenance mentioned above, and thus will not be described again herein.

Similarly, a method for applying or administering the preparation for skin care and/or maintenance in the method for promoting collagen proliferation, growth factor secretion, and/or cytokine secretion of the present disclosure mentioned above may be oral, parenteral by an inhalation spray, or via an implanted reservoir to a subject. The oral compositions and parenteral methods for applying or administering the preparation for promoting collagen proliferation, growth factor secretion, and/or cytokine secretion may be the same as those for the biomedical composition which can be used in the manufacture of a preparation for promoting collagen proliferation, growth factor secretion, and/or cytokine secretion mentioned above and will not be described again herein.

Moreover, the subject in the method for promoting collagen proliferation, growth factor secretion, and/or cytokine secretion of the present disclosure mentioned above may include, but is not limited to, a vertebrate. The vertebrate mentioned above may include a fish, an amphibian, a reptile, a bird, or a mammal, but it is not limited thereto. Examples of mammals include, but are not limited to, a human, an orangutan, a monkey, a horse, a donkey, a dog, a cat, a rabbit, a guinea pig, a rat, and a mouse. In one embodiment, the subject is a human.

In addition, the present disclosure provides a biomedical composition, which can be used in the manufacture of a preparation for delaying and/or inhibiting skin aging. Accordingly, the present disclosure also provides a method for delaying and/or inhibiting skin aging, and the method for skin care and/or maintenance may comprise, but is not limited to applying or administering a preparation for delaying and/or inhibiting skin aging to a subject, wherein the preparation comprises a biomedical composition.

The biomedical composition mentioned above may comprise, but is not limited to, an effective amount of micelle, and furthermore, the micelle may comprise a hyaluronic acid and/or a derivative thereof and a modified histidine. The modified histidine mentioned above is grafted to at least one primary hydroxyl group of the hyaluronic acid and/or the derivative thereof, and the graft ratio is 1-100%. Moreover, the foregoing hyaluronic acid and/or the derivative thereof and the modified histidine form the foregoing micelle on a weight percentage of 0.2-300:1. The biomedical composition mentioned above may be further used in combination with at least one antioxidant, and the biomedical composition coats the at least one antioxidant in the form of the micelle.

In the biomedical composition which can be used in the manufacture of a preparation for delaying and/or inhibiting skin aging of the present disclosure mentioned above, the antioxidant may comprise, but is not limited to, vitamin C (or ascorbic acid), proanthocyanidins, glutathione (GSH), lipoic acid (Lipoic). Acid), astaxanthin, vitamin E (or vitamin E, Vitamin E), β-carotene, coenzyme Q, isoflavones, or any combination thereof. For example, in one embodiment, the antioxidant may be vitamin C. In another embodiment, the antioxidant may be a carotenoid, such as β-carotene. In another embodiment, the antioxidant can be a combination of vitamin C and β-carotene. In another embodiment, the antioxidant can be a combination of vitamin C, β-carotene and astaxanthin.

In the biomedical composition which can be used in the manufacture of a preparation for delaying and/or inhibiting skin aging of the present disclosure mentioned above, the weight ratio of the effective amount of the micelle to the at least one antioxidant may be about 0.1-500. In one embodiment, the weight ratio of the effective amount of the micelle to the at least one antioxidant may be about 0.2-5, 0.5-10, 1-20, 5-50, 10-100, 20-120, 30-150, 50-200, 80-250, 100-300, 150-350, 200-400, 250-450, 300-500, but it is not limited thereto. In another embodiment, the weight ratio of the effective amount of the micelle to the at least one antioxidant may be about 0.5-500, 1-300, 5-250, 10-200, 20-180, 30-150, 40-120, 50-100, but it is not limited thereto. In another embodiment, the weight ratio of the effective amount of micelles to the at least one antioxidant is from 0.5-5. In another embodiment, the weight ratio of the effective amount of micelles to the at least one antioxidant may be 1-20. In another embodiment, the weight ratio of the effective amount of micelles to the at least one antioxidant may be 2-15.

Furthermore, in the above-mentioned biomedical composition of the present disclosure which can be used in the manufacture of a preparation for delaying and/or inhibiting skin aging, the types of pharmaceutically acceptable carriers or salts, and an applying/administration technique for the biomedical composition can be the same as those for those for the biomedical composition which can be used in the manufacture of a preparation for skin care and/or maintenance mentioned above, and thus will not be described again herein.

Similarly, a method for applying or administering the preparation for delaying and/or inhibiting skin aging in the method for delaying and/or inhibiting skin aging of the present disclosure mentioned above may be oral, parenteral by an inhalation spray, or via an implanted reservoir to a subject. The oral compositions and parenteral methods for applying or administering the preparation for delaying and/or inhibiting skin aging may be the same as those for the biomedical composition which can be used in the manufacture of a preparation for promoting collagen proliferation, growth factor secretion, and/or cytokine secretion mentioned above and will not be described again herein.

Moreover, the subject in the method for delaying and/or inhibiting skin aging of the present disclosure mentioned above may include, but is not limited to, a vertebrate. The vertebrate mentioned above may include a fish, an amphibian, a reptile, a bird, or a mammal, but it is not limited thereto. Examples of mammals include, but are not limited to, a human, an orangutan, a monkey, a horse, a donkey, a dog, a cat, a rabbit, a guinea pig, a rat, and a mouse. In one embodiment, the subject is a human.

The present disclosure further provides a biomedical composition that may comprise, but is not limited to, a hyaluronic acid and/or a derivative thereof, a modified histidine, and at least one antioxidant. The modified histidine mentioned above is grafted to at least one primary hydroxyl group of the hyaluronic acid and/or the derivative thereof, and the graft ratio is 1-100%. Moreover, the foregoing hyaluronic acid and/or the derivative thereof and the modified histidine form the foregoing micelle on a weight percentage of 0.2-300:1, and the effective amount of the microcell can further form the biomedical composition with at least one antioxidant by the weight ratio of about 0.1-500.

In the biomedical composition or the biomedical composition which can be used in the manufacture of a preparation for delaying and/or inhibiting skin aging of the present disclosure mentioned above, examples of suitable hyaluronic acid derivatives, grafting ratio of modified histidine to hyaluronic acid and/or its derivatives, molecular weight of hyaluronic acid and/or its derivatives, examples of suitable modified histidine, examples of suitable antioxidant and the like are further disclosed in the above description, and will not be further described herein.

Moreover, the biomedical composition or the biomedical composition which can be used in the manufacture of a preparation for delaying and/or inhibiting skin aging of the present disclosure mentioned above, the percentage by weight of both of hyaluronic acid and/or a derivative thereof and the modified histidine for forming the micelle, a particle size of micelle formed by hyaluronic acid and/or a derivative thereof and modified histidine, the percentage by weight of an effective amount of micelle to the overall biomedical composition, the weight ratio of the effective amount of the micelle to the at least one antioxidant and the like are further disclosed in the above description, and will not be further described herein.

Furthermore, in the above-mentioned biomedical composition of the present disclosure, or a biomedical composition which can be used in the manufacture of a preparation for delaying and/or inhibiting skin aging, the kind of the pharmaceutically acceptable carrier or salt, and the technique of administration of the biomedical composition are also further disclosed in the above description, and thus will not be described again herein.

EXAMPLES

A. Materials and Methods

1. Preparation of Material 1: Preparation of Hyaluronic Acid Micelle I

First, hyaluronic acid ($HA_{38K}$) having a molecular weight of 38,000 Dalton was prepared to $HA_{38K}$ with a concentration of about 0.75 mM using tetrabutylammonium as a solvent. After 3 hours of reaction at room temperature (about 20-25° C.), the preparation of HA Micelle precursor ($HA_{38K}$-pre) was completed.

Next, $HA_{38K}$-pre was added in dimethylacetamide (DMAC) and mixed by stirring. At this time, the concentration of $HA_{38K}$-pre was about 0.36 mM. After $HA_{38K}$-pre was completely dissolved, about 2-3% percentage by weight of Boc-histidine was added. At the same time, mixing was performed continuously until the solution was uniform, and then water removal was performed by vacuum, and about 1-2% percentage by weight of 1-ethyl-3-(3-dimethylaminopropyl)carbodiimide (EDC, a water-soluble carbodiimide, often in the form of the hydrochloride) was added to perform an activation reaction in which $HA_{38K}$-pre: Boc-histidine: EDC were reacted in a mixing ratio of 1:1.2:1 to form a mixture. After 40 hours of reaction, the mixture was filtered and purified by a filter bag (Size: 50 μm) and a dialysis membrane (Size: 10 kD; Brand: Sartorius), wherein the pressure difference between the inlet and the outlet of the dialysis pump was set to 2.5 bar. After that, histidine-modified hyaluronic acid micelle I (HA Micelle I) with Na ion was obtained by ion exchange resin ($Na^+$ resin), and the graft ratio was 33.3%.

2. Preparation of Material 2: Preparation of Hyaluronic Acid Micelle II

First, hyaluronic acid ($HA_{16K}$) having a molecular weight of 16,000 Dalton was prepared to $HA_{16K}$ with a concentration of about $1.79 \times 10^{-3}$ M using tetrabutylammonium as a solvent. After 3 hours of reaction at room temperature (about 20-25° C.), the preparation of HA Micelle precursor ($HA_{16K}$-pre) was completed.

Next, $HA_{16K}$-pre was added in dimethylacetamide (DMAC) and mixed by stirring. At this time, the concentration of $HA_{16K}$-pre was about 0.36 mM. After $HA_{38K}$-pre was completely dissolved, about 2-3% percentage by weight of Boc-histidine was added. At the same time, mixing was performed continuously until the solution was uniform, and then water removal was performed by vacuum, and about 1-2% percentage by weight of 1-ethyl-3-(3-dimethylaminopropyl)carbodiimide (EDC) was added to perform an activation reaction in which $HA_{16K}$-pre: Boc-histidine: EDC were reacted in a mixing ratio of 1:2.2:1 to form a mixture. After 40 hours of reaction, the mixture was filtered and purified by a filter bag (Size: 50 μm) and a dialysis membrane (Size: 10 kD; Brand: Sartorius), wherein the pressure difference between the inlet and the outlet of the dialysis pump was set to 1 bar. After that, histidine-modified hyaluronic acid micelle II (HA Micelle II) with Na ion was obtained by ion exchange resin ($Na^+$ resin), and the graft ratio was 89.0%.

3. Preparation of Material 3: Preparation of Hyaluronic Acid Micelle III

First, hyaluronic acid ($HA_{16K}$) having a molecular weight of 16,000 Dalton was prepared to $HA_{16K}$ with a concentration of about $1.79 \times 10^{-3}$ M using tetrabutylammonium as a solvent. After 3 hours of reaction at room temperature (about 20-25° C.), the preparation of HA Micelle precursor ($HA_{16K}$-pre) was completed.

Next, $HA_{16K}$-pre was added in dimethylacetamide (DMAC) and mixed by stirring. At this time, the concentration of $HA_{16K}$-pre was about 0.36 mM. After $HA_{38K}$-pre was completely dissolved, about 2-3% percentage by weight of Boc-histidine was added. At the same time, mixing was performed continuously until the solution was uniform, and then water removal was performed by vacuum, and about 1-2% percentage by weight of 1-ethyl-3-(3-dimethylaminopropyl)carbodiimide (EDC) was added to perform an activation reaction in which $HA_{16K}$-pre: Boc-histidine: EDC were reacted in a mixing ratio of 1:1.1:1 to form a mixture. After 40 hours of reaction, the mixture was filtered and purified by a filter bag (Size: 50 μm) and a dialysis membrane (Size: 10 kD; Brand: Sartorius), wherein the pressure difference between the inlet and the outlet of the dialysis pump was set to 1 bar. After that, histidine-modified hyaluronic acid micelle II (HA Micelle II) with Na ion was obtained by ion exchange resin ($Na^+$ resin), and the graft ratio was 21.0%.

4. Preparation of Material 4: Preparation of Hyaluronic Acid Micelle IV

First, hyaluronic acid ($HA_{16K}$) having a molecular weight of 16,000 Dalton was prepared to $HA_{16K}$ with a concentration of about $1.79 \times 10^{-3}$ M using tetrabutylammonium as a solvent. After 3 hours of reaction at room temperature (about 20-25° C.), the preparation of HA Micelle precursor (HA$_{16K}$-pre) was completed.

Next, HA$_{16K}$-pre was added in dimethylacetamide (DMAC) and mixed by stirring. At this time, the concentration of HA$_{16K}$-pre was about 0.36 mM. After HA$_{38K}$-pre was completely dissolved, about 2-3% percentage by weight of Boc-histidine was added. At the same time, mixing was performed continuously until the solution was uniform, and then water removal was performed by vacuum, and about 1-2% percentage by weight of 1-ethyl-3-(3-dimethylaminopropyl)carbodiimide (EDC) was added to perform an activation reaction in which HA$_{16K}$-pre: Boc-histidine: EDC were reacted in a mixing ratio of 1:1.1:1 to form a mixture. After 40 hours of reaction, the mixture was filtered and purified by a filter bag (Size: 50 μm) and a dialysis membrane (Size: 10 kD; Brand: Sartorius), wherein the pressure difference between the inlet and the outlet of the dialysis pump was set to 2.5 bar. After that, histidine-modified hyaluronic acid micelle II (HA Micelle II) with Na ion was obtained by ion exchange resin (Na$^+$ resin), and the graft ratio was 17.0%.

5. Material Preparation 5: Preparation of an Essence Formula with 1 wt % HA Micelle 1-5 g of panthenic acid (dexpanthenol), 0.1-0.5 g of allantoin and 2-5 g of glycerin were added to 75-90 ml of deionized/demineralized water and stirred at 25-35° C. for 3-6 hours until evenly mixed as a base formula of an essence. After that, 1 wt % of HA Micelle was added to the base formula of the above essence to form an essence formula with 1 wt % HA Micelle.

6. Preparation of Material 6: Preparation of HA Micelle Coated-Vitamin C (Ascorbic Acid)

0.1 mg of vitamin C was added to 10 ml of deionized pure water, and uniformly mixed at room temperature (about 20-25° C.) to prepare a vitamin C stock solution with a concentration of 10 μg/ml. Next, the 10 μg/ml vitamin C stock solution mentioned above was mixed with 10 μg/ml, 100 μg/ml and 500 μg/ml HA Micelle at room temperature to form HA Micelle coated-vitamin C, respectively, wherein ratios of vitamin C to HA Micelle with different concentrations (10 μg/ml, 100 μg/ml, 500 μg/ml) were vitamin C: HA Micelle=1:1, 1:10, 1:50, respectively.

7. Preparation of Material 7: Preparation of HA Micelle Coated-β-Carotene 8 mg of β-carotene was uniformly dissolved in 10 ml of 99.9% ethanol at room temperature to prepare a β-carotene stock solution with a concentration of 800 μg/ml. Next, the 800 μg/ml β-carotene stock solution mentioned above was mixed with 800 μg/ml, 4 mg/ml and 8 mg/ml HA Micelle at room temperature to form a HA Micelle coated-β-carotene, wherein ratios of β-carotene to HA Micelle with different concentrations (800 μg/ml, 4 mg/ml, 8 mg/ml) was β-carotene: HA Micelle=1:1, 1:5, 1:10, respectively.

8. Method 1: Assay of Inducing Secretion of Growth Factor or Cytokine Associated with Wound Healing by HA Micelle This in vitro assay was performed using an HSF cell strain of human skin fibroblast purchased from the Agricultural Technology Research Institute, Animal Technology Laboratories.

The human skin fibroblast cell line HSF mentioned above was inoculated into a 6-well cell culture plate containing cell culture solution (DMEM, brand Gibco) at 3×10$^5$ cells/well. After cell attachment, 0.3 wt % A hyaluronic acid (HA), 0.3 wt % HA Micelle and 0.075 wt % HA Micelle were respectively added to the cells for co-culture while no addition was used as a control group.

After 7 days of co-culture, supernatant of each well was collected and secretion amounts of IL-1β, PDGF, FGF, IL-8 and GM-CSF were analyzed by various enzyme-linked immunosorbent assay kits for secretions of growth factors or cytokines related to wound healing, comprising: IL-1βELISA Kit (Bio-Plex Pro™), PDGF ELISA Kit (Bio-Plex Pro™), FGF ELISA Kit (Bio-Plex Pro™), IL-8 ELISA Kit (Bio-Plex Pro™) and GM-CSF ELISA Kit (Bio-Plex Pro™) according to the instruction of each kit.

9. Method 2: Assay of Inducing Collagen Proliferation by HA Micelle

Similarly, this in vitro assay was also performed using an HSF cell strain of human skin fibroblast purchased from the Agricultural Technology Research Institute, Animal Technology Laboratories.

The human skin fibroblast cell line HSF mentioned above was inoculated into a 6-well cell culture plate containing cell culture solution (DMEM, brand Gibco) at 3×10$^5$ cells/well. After cell attachment, 0.25 wt % HA Micelle and 0.06 wt % HA Micelle were respectively added to the cells for co-culture while no addition was used as a control group.

After 7 days of co-culture, supernatant of each well was collected and secretion amounts of collagen were analyzed by Collagen Assay Kit (Specification S1000, brand Biocolor) according to the instruction of the kit.

10. Method 3: Assay for Human Skin by HA Micelle

The in vivo skin assay was performed on 28 subjects (9 males and 19 females) with an average age of 40.5±9.8 years using the above-mentioned essence formula containing 1 wt % HA Micelle. The base formula without HA Micelle addition was used as a placebo to apply to the control group.

After applying the above-mentioned essence containing 1 wt % HA Micelle to the face for 28 consecutive days, the skin condition of the 28 subjects were examined and analyzed by the following various analyzers: a skin water content meter (CK Corneometer®; Model: CM825; Brand: Courage+Khazaka electronic GmbH) was used to detect skin hydration, a skin transepidermal water loss rate meter (CK Tewameter®; Model: TM300; Brand: Courage+Khazaka electronic GmbH) was used to detect the degree of water loss through skin, a skin elasticity meter (CK Cutometer®; Model: MPA580; Brand: Courage+Khazaka electronic GmbH) was used to detect skin elasticity, an ultrasonic analyzer (Model: DermaLab®; Brand: Cortex Technology) was used to perform an ultrasonic test on skin, and a full face skin analyzer (CK VisioFace® RD; Model: VisioFace® RD; Brand: Courage+Khazaka electronic GmbH) was used to analyze skin roughness and skin pore size.

11. Method 4: Antioxidant Degradation Evaluation Assay

This assay was performed according to a method modified from the method shown by Roberts et al. (1997). First, a liquid sample containing a specific antioxidant at a concentration to be tested was prepared, and the liquid sample containing the specific antioxidant was added into a 250 mL Erlenmeyer flask by a pipette and deionized water was added the to the Erlenmeyer flask to reach the 100 mL scale mark. At the same time, 1 mL of 0.1 M sodium iodide (NaI) and 1 mL of 0.1 M hydrochloric acid (hydrogen chloride, HCl) and 1 mL of 2% starch aqueous solution (indicator) were added to the Erlenmeyer flask. Next, a burette was rinsed the with 0.025 M potassium iodate (KIO$_3$) at least twice, first, and then filled with 0.025 M potassium iodate in a technique of avoiding bubble formation during the filling, and the initial volume of the solution (V$_i$) in the burette was record after the filling. Thereafter, the liquid sample containing the specific antioxidant mentioned above was titrated with 0.025 M potassium iodate. When the solution appeared blue and did not fade, the titration end point was reached, and the final titration volume ($V_f$) was needed to be recorded. Depending on the condition, the titration operation mentioned above could be repeated two or three times, as appropriate. Finally, the specific antioxidant content could be calculated from the titration volume of potassium iodate.

12. Method 5: ABTS Free Radical Scavenging Assay

Antioxidant capacity of a sample to be tested was evaluate by ABTS (English full name: 2,2'-azinobis-3-ethyl benzothiazoline-6-sulphonic acid) free radical scavenging test. Since ABTS and potassium persulphate ($K_2S_2O_8$) will produce an oxidation reaction and form a stable blue-green water-soluble ABTS•+ radical ion with a maximum absorption peak at 734 nm, ABTS•+ free radical concentration can be detected through $A_{734}$ nm. When the ABTS•+ radical solution is added with an antioxidant (radical scavenger), the original single radicals are paired, causing the ABTS•+ radical solution to fade and the $A_{734}$ nm absorption value to decrease, thereby evaluating Free radical scavenging ability of the antioxidant can be evaluated.

This assay was performed according to a method modified from the method shown by Arnao et al. (1996). ABTS (Factory Sigma) was dissolved in deionized water (DI water) at room temperature and adjusted to a concentration of 7 mM, and then 2.45 mM potassium persulfate was added therein to form a mixed solution. The mixed solution was placed in a dark room at room temperature for 16 hours of reaction to form stable ABTS•+ radical ions (blue-green), and then the mixed solution was diluted with deionized water to form a ABTS•+ radical ion working solution with absorbance of 0.75±0.05 at 734 nm by a spectrophotometer.

Next, a sample to be tested and standards (Trolox) with different concentrations were added to the ABTS•+ radical ion working solution, respectively, and a group in which only deionized water was added was used as a control group. Absorbance at 734 nm was detected by a spectrophotometer after 20 minutes of reaction. Abilities to scavenge ABTS•+ radicals of the standards (Trolox) with different concentrations were plotted as a scavenging standard curve. The measured absorbance of the sample to be tested and the control group are converted according to the standard curve to know the free radical scavenging ability of the sample to be tested. The formula for calculating the scavenging ability is: $(1-ABS_{sample}/ABS_{control}) \times 100$.

13. Method 6: DPPH Free Radical Scavenging Assay

Antioxidant capacity of a sample to be tested was evaluate by DPPH (English full name: 1,1-diphenyl-2-picrylhydrazyl) free radical scavenging test. DPPH is a stable free radical. When it is dissolved in methanol or ethanol, it will appear purple and has a strong absorbance at 515 nm. When the sample to be tested can directly react with DPPH radicals, it will block the shackle reaction of DPPH free radicals. At this time, the DPPH solution which originally appeared blue-violet will turn into clear yellow, and the absorbance at 515 nm will decrease, and that means that the sample to be tested has an antioxidant component that captures DPPH free radicals. The lighter the color become, the stronger ability to capture DPPH free radicals the antioxidant component has, which means the better the antioxidant capacity of the sample to be tested has.

This assay was performed according to a method modified from the method shown by Parejo et al (2003). Aqueous solution of the sample to be tested and standards (Glutathione) with different concentrations each 30 µl were added to the 96-well plate, respectively, and water was used as a blank control. Thereafter, 120 µl of 100 mM Tris-HCl buffer (pH 7.4) was added to the plate and then 150 µl of 500 µM DPPH (Sigma Sigma) ethanol solution was immediately added and uniformly mixed at room temperature and allowed to stand in the dark for 20 minutes. After that, absorbance at 515 nm was detected by a spectrophotometer. The more DPPH free radicals were scavenged, the more the absorbance value decreased. Ability of each sample to be tested to scavenge DPPH free radicals (also means the strength of the hydrogen supply capacity of the sample to be tested) can be determined by percentage of decrease in absorbance relative to the blank control group.

B. Results

1. Effect of HA Micelle on Secretion of Growth Factor or Cytokine Associated with Wound Healing It is currently known that cells located near the wound promote regeneration and remodeling of wound tissue by increasing the secretion of related growth factors and cytokines. There are quite a lot of growth factors and cytokines involved in this process, such as: (1) PDGF (Platelet-derived growth factor), which regulates cell growth and differentiation and plays an important role in angiogenesis; (2) FGF (Fibroblast Growth Factor) associated with angiogenesis, cell migration and proliferation, and various cell differentiation (including fibroblasts and epidermal cells); (3) GM-CSF (granulocyte-macrophage colony stimulating factor) capable of stimulating bone marrow stem cell to form colony composed granules and mononuclear macrophages, capable of promoting proliferation, differentiation and maturation of progenitor cells of neutrophils and macrophage, and capable of promoting healing of wound of burns and chronic ulcer; (4) IL-1β (Interleukin-1 beta, belong to a class of interleukin-1) capable of regulating or triggering an initial inflammatory response, and as an immunoregulatory factor; and (5) IL-8 (Interleukin-8) capable of promoting angiogenesis and has cellular chemotaxis to neutrophils.

In order to determine the induction effect of HA Micelle on the secretions of the growth factors and cytokine mentioned above, the "Preparation of Material 1-4: Preparation of Hyaluronic Acid Micelles I-IV" and "8. Method 1: Assay of inducing secretion of growth factor or cytokine associated with wound healing by HA Micelle" is used to test the effects of simple HA (HA Micelle was not formed), 0.3 wt % HA Micelle and 0.075 wt % HA Micelle on GM-CSF, IL-1β and IL-8 PDGF, FGF secretions of human skin fibroblast strain HSF. The results are shown in Table 1.

TABLE 1

Effect of HA Micelle on secretion of growth factor or cytokine associated with promotion of wound healing.

| Growth factor or cytokine | Group | HA content (wt %) | Secretion amount (pg/ml) | Ratio (compared to the control group) |
|---|---|---|---|---|
| PDGF | Control group | 0 | 1.67 | — |
| | HA | 0.3 | 2.08 | 1.25 |
| | HA Micelle | 0.3 | 3.71 | 2.23 |
| | HA Micelle | 0.075 | 2.17 | 1.30 |
| FGF | Control group | 0 | 9.87 | — |
| | HA | 0.3 | 16.15 | 1.64 |
| | HA Micelle | 0.3 | 21.29 | 2.16 |
| | HA Micelle | 0.075 | 11.58 | 1.17 |
| GM-CSF | Control group | 0 | 7.10 | — |
| | HA | 0.3 | 11.85 | 1.67 |
| | HA Micelle | 0.3 | 87.72 | 12.35 |
| | HA Micelle | 0.075 | 22.35 | 3.15 |

TABLE 1-continued

Effect of HA Micelle on secretion of growth factor or cytokine associated with promotion of wound healing.

| Growth factor or cytokine | Group | HA content (wt %) | Secretion amount (pg/ml) | Ratio (compared to the control group) |
|---|---|---|---|---|
| IL-1β | Control group | 0 | 0.37 | — |
| | HA | 0.3 | 0.54 | 1.45 |
| | HA Micelle | 0.3 | 1.12 | 3.00 |
| | HA Micelle | 0.075 | 0.62 | 1.66 |
| IL-8 | Control group | 0 | 274.79 | — |
| | HA | 0.3 | 865.16 | 3.15 |
| | HA Micelle | 0.3 | 4947.48 | 18.00 |
| | HA Micelle | 0.075 | 1939.01 | 7.06 |

As shown in Table 1, since HA is known as one of the most common wound care materials, simple HA alone (HA Micelle was not formed) already had an ability to promote growth factor and cytokine secretion, while the promotion of modified HA Micelle for growth factors and cytokines secretion was more significant and positively correlated with the occupied proportion of HA.

Under the induction of 0.3 wt % HA Micelle, the secretions of GM-CSF and IL-8 was more than 10 times compared with the control group, indicating that HA Micelle could indeed promote skin fibroblasts to secret growth factors and cytokines, and promote matrix reconstruction and tissue reconstruction near the wound by these growth factors and cytokines to achieve the effect of acceleration of wound healing.

2. Effect of HA Micelle on Collagen Proliferation

Collagen is known as an important protein in the human body, accounting for 25~35% of total human protein, mainly in connective tissue, and also a major component of extracellular matrix and skin. Collagen in the skin mainly exists in the dermis layer, providing support and protection, maintaining skin elasticity and strength, having functions of improving skin hydration and oil balance, and having effects of delaying aging and repairing skin scars. When the human skin begins to age, the rate of fibroblasts proliferating collagen will also decrease, gradually causing the rate of collagen production in the skin to be less than the rate of loss, and the skin gradually loses its elasticity.

In order to determine the induction effect of HA Micelle on collagen proliferation, the "Preparation of Material 1-4: Preparation of Hyaluronic Acid Micelles I-IV" and "9. Method 2: Assay of inducing collagen proliferation by HA Micelle" were used to test the effects of 0.25 wt % HA Micelle and 0.06 wt % HA Micelle on collagen secretion amount of human skin fibroblast strain HSF. The results are shown in FIG. 1.

As shown in FIG. 1, the addition of HA Micelle to human skin fibroblast strain HSF and co-culture do promote collagen proliferation and is positively correlated with the percentage of HA Micelle added. The addition of 0.25 wt % HA Micelle can make secretion of collagen reach more than 50% of proliferation effect, while the addition of 0.06 wt % HA Micelle can also make can make secretion of collagen reach more than 25% of proliferation effect.

3. Effect of HA Micelle on Human Skin

It is known that there are many causes of skin aging. In addition to the loss of collagen mentioned above, denaturation and reduction of elastic fibers in the dermis layer are also one of the most important causes, and that will cause the skin to lose elasticity and strength. Moreover, the aging of the skin will cause the thickness of the epidermis and dermis to become thinner, and that causes the water content of the stratum corneum of the skin to decrease, the hydration to decrease, and thus the skin will be dry, rough and wrinkled. Furthermore, when the collagen and elastic fibers in the skin around the skin pores are gradually lost and cannot support the skin pore structure, the skin pores begin to collapse around, and the pores themselves are coarse and loose.

Therefore, the degree of skin aging can be initially known by examining characterizations or properties of the skin hydration, the degree of water loss through (degree of water retention), skin elasticity, skin roughness, and pore size, etc.

In order to determine the maintenance and care effect of HA Micelle on the above-mentioned characterizations or properties of human skin, "5. Material Preparation 5: Preparation of an essence formula with 1 wt % HA Micelle" and "10. Method 3: Assay for human skin by HA Micelle" mentioned above were used to determine the effect of an essence formula with 1 wt % HA Micelle on subjects with an average age of 40.5±9.8 years. The results are shown in Table 2.

TABLE 2

Effect of HA Micelle on human skin

| Test item | Control group | Experimental group |
|---|---|---|
| Skin hydration | 1.9% | 15.7% |
| Skin firmness | 3.0% | 18.9% |
| Pore shrinkage | 12.4% | 27.7% |
| Collagen density | 1.9% | 30.1% |
| Rough skin improvement | 23.2% | 44.7% |
| Skin water retention rate | 1.5% | 16.0% |

As shown in Table 2, compared with the control group in which only the base formulation was administered, the experimental group in which an essence formula with 1 wt % HA Micelle was administered for 28 consecutive days shows excellent results in all skin testing items. In particular, the collagen density of the experimental group is increased by 30.1% after 28 days while the control group is only increased by 1.9%, and the skin hydration and water retention rate of the experimental group is increased by 15.7% and 16.0%, respectively while the control group is only increased 1.9% and 1.5%, respectively. In addition, compared with the control group in which the skin firmness of the subjects is increased by 3.0%, the pore shrinkage degree of the subjects is improved by 12.4%, and the skin roughness of the subjects is improved by 23.2%, the experimental group shows that the skin firmness of the subjects is increased by 18.9%, the pore shrinkage degree of the subjects is improved by 27.7% and the skin roughness is improved by 44.7%. It is shown that the continuous administration of the essence formula with 1 wt % HA Micelle can actually achieve an effect of improving the skin texture of the human body.

4. Effect of HA Micelle on Vitamin C Coated Thereby

Vitamin C, also known as L-ascobic acid, is a good reducing agent and an essential nutrient for higher primates and other minority creatures. Most mammals can synthesize vitamin C by liver by themselves, but humans and primates cannot synthesize vitamin C by themselves and have to ingest it through food, and in the absence of vitamin C, scurvy can be caused. Vitamin C is involved in many functions in the body, such as the ability to protect the body from threat from oxidants, and thus it can be considered an antioxidant. At the same time, vitamin C also contributes to tissue repair and promotes collagen synthesis and strengthens its structure. However, vitamin C is water-soluble and is easily damaged by high temperature, resulting in its own instability.

In order to evaluate the protective effect of HA Micelle on the vitamin C coated thereby, "6. Preparation of Material 6: Preparation of HA Micelle coated-vitamin C (ascorbic acid)" and "11. Method 4: Antioxidant degradation evaluation assay" mentioned above were used to examine the protective effects of HA Micelle with different concentrations (10 μg/ml, 100 μg/ml, 500 μg/ml) on vitamin C at room temperature (about 26° C.). The results are shown in FIG. 2.

Figure 2:
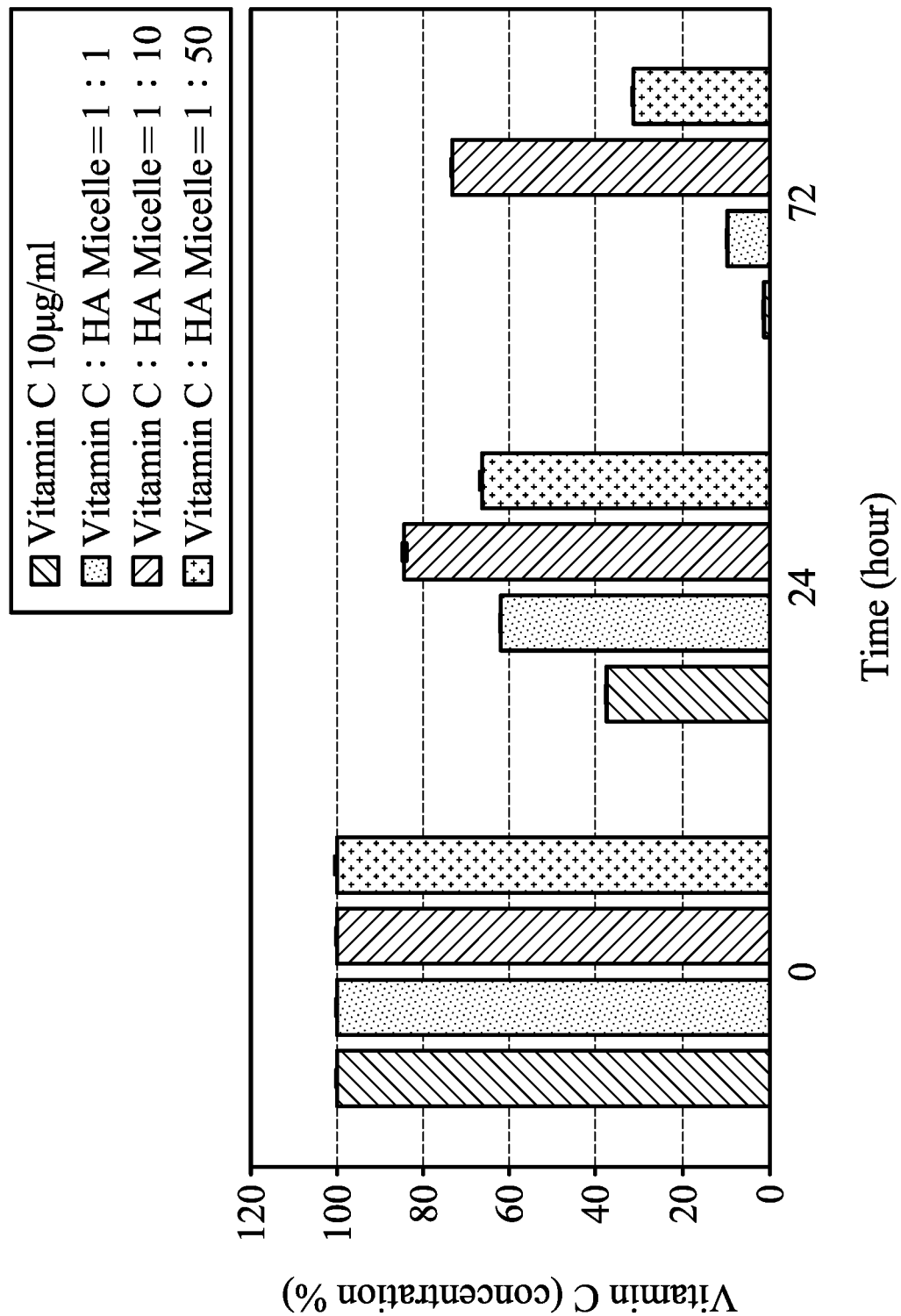
FIG. 2 shows the effect of HA micelle on the concentration of vitamin C coated thereby at room temperature.

As shown in FIG. 2, the concentration of vitamin C decreases to about 40% of the initial concentration (reduced 62.6%) after being placed in the normal temperature state for 24 hours, and is almost completely degraded after being left to 72 hours (only remains about 0.9% of the initial concentration). In contrast, the degradation rate of vitamin C coated with HA Micelle has a tendency to slow down. The coating ratio of vitamin C:HA Micelle=1:10 has better protection to vitamin C, wherein after being placed in the normal temperature state for 24 hours, it only is only degraded by 15.8%, and maintained a concentration of about 70% of the initial concentration in 72 hours (73.2%). It shows that HA Micelle has a protective effect on the vitamin C coated thereby at normal temperature and can obviously slow down the decomposition rate of vitamin C.

5. Effect of HA Micelle on vitamin C coated thereby at high temperature

In order to evaluate whether HA Micelle still has a protective effect on the vitamin C coated thereby at a high temperature, similarly, "6. Preparation of Material 6: Preparation of HA Micelle coated-vitamin C (ascorbic acid)" and "11. Method 4: Antioxidant degradation evaluation assay" mentioned above were used to examine the protective effect of HA Micelle with different concentrations (10 μg/ml, 100 μg/ml, 500 μg/ml) on vitamin C at high temperature (about 40° C.). The results are shown in FIG. 3.

Figure 3:
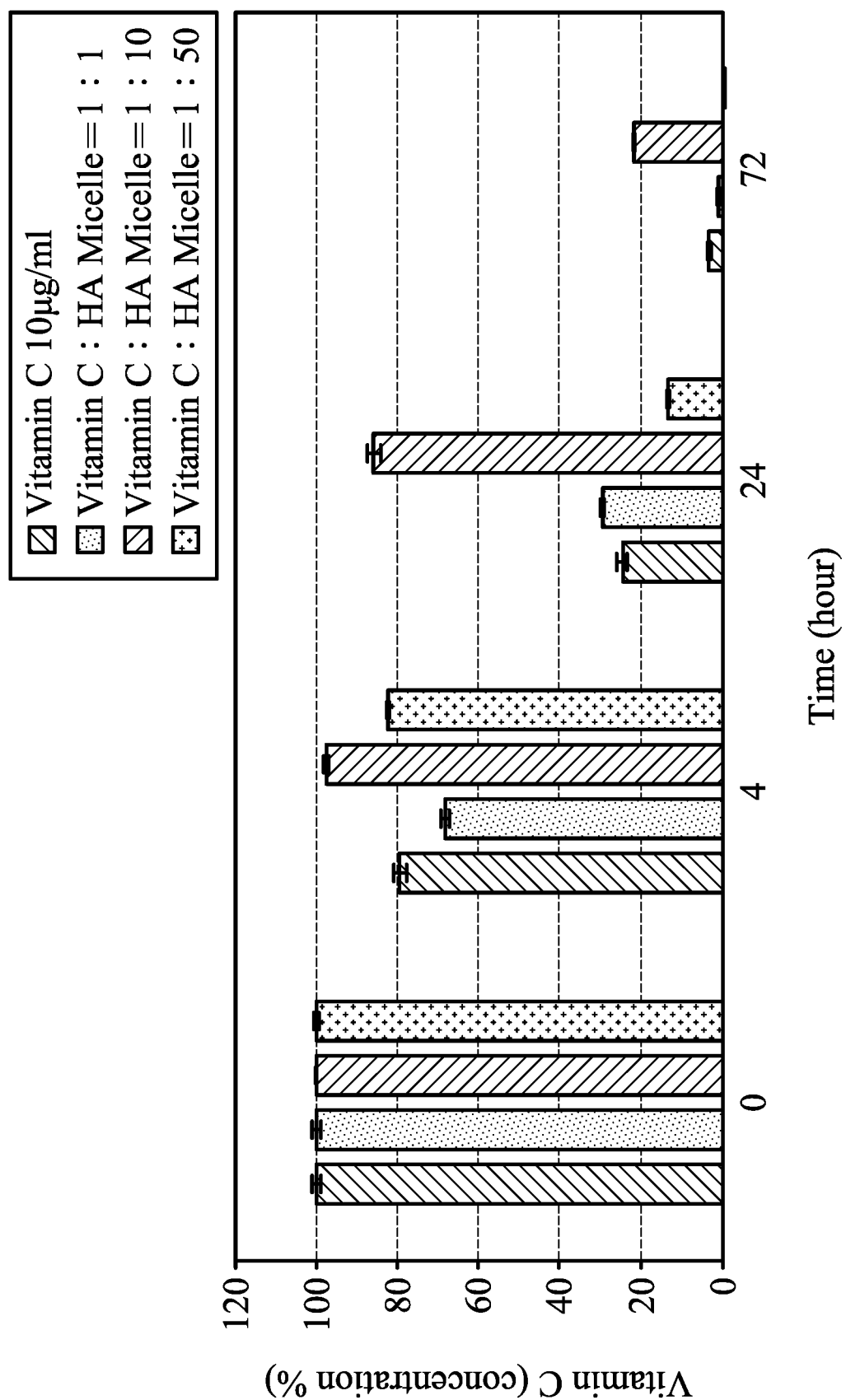
FIG. 3 shows the effect of HA micelles on the concentration of vitamin C coated thereby at a high temperature.

As shown in FIG. 3, vitamin C decreased by 20.4% when only being placed at 40° C. for 4 hours, and remains about 24.3% of the initial concentration when continuously being placed at 40° C. to 24 hours, and vitamin C degraded to only 3.3% of the initial concentration after being left to 72 hours. In contrast, the degradation rate of vitamin C coated with HA Micelle at high temperature of about 40° C. still has a tendency to slow down. Similarly, the coating ratio of vitamin C:HA Micelle=1:10 has better protection to vitamin C, wherein after being placed at 40° C. for 4 hours, it is almost maintained at the initial concentration, and after being left to 24 hours, it only degraded by 14.1%, and still has 21.8% of the initial concentration even after being placed at 40° C. for 72 hours. It shows that HA Micelle still has a protective effect on the vitamin C coated thereby even at high temperature and can obviously slow down the decomposition rate of vitamin C. Conversely, the decomposition rate of vitamin C which is not coated with HA Micelle, is very fast at high temperatures, and it is cleaved to remain 20% in only one day.

6. Size Change of HA Micelle Before and after Coating Antioxidant

In order to examine whether HA Micelle has a change in particle size after coating an antioxidant (for example, vitamin C), particle sizes of HA Micelle of "6. Preparation of Material 6: Preparation of HA Micelle coated-vitamin C (ascorbic acid)" before and after coating vitamin C are detected by a Laser Diffraction Particle Size Analyzer (Malvern). The result is a particle size distribution by dynamic light scattering (DLS) as shown in FIG. 4.

Figure 4:
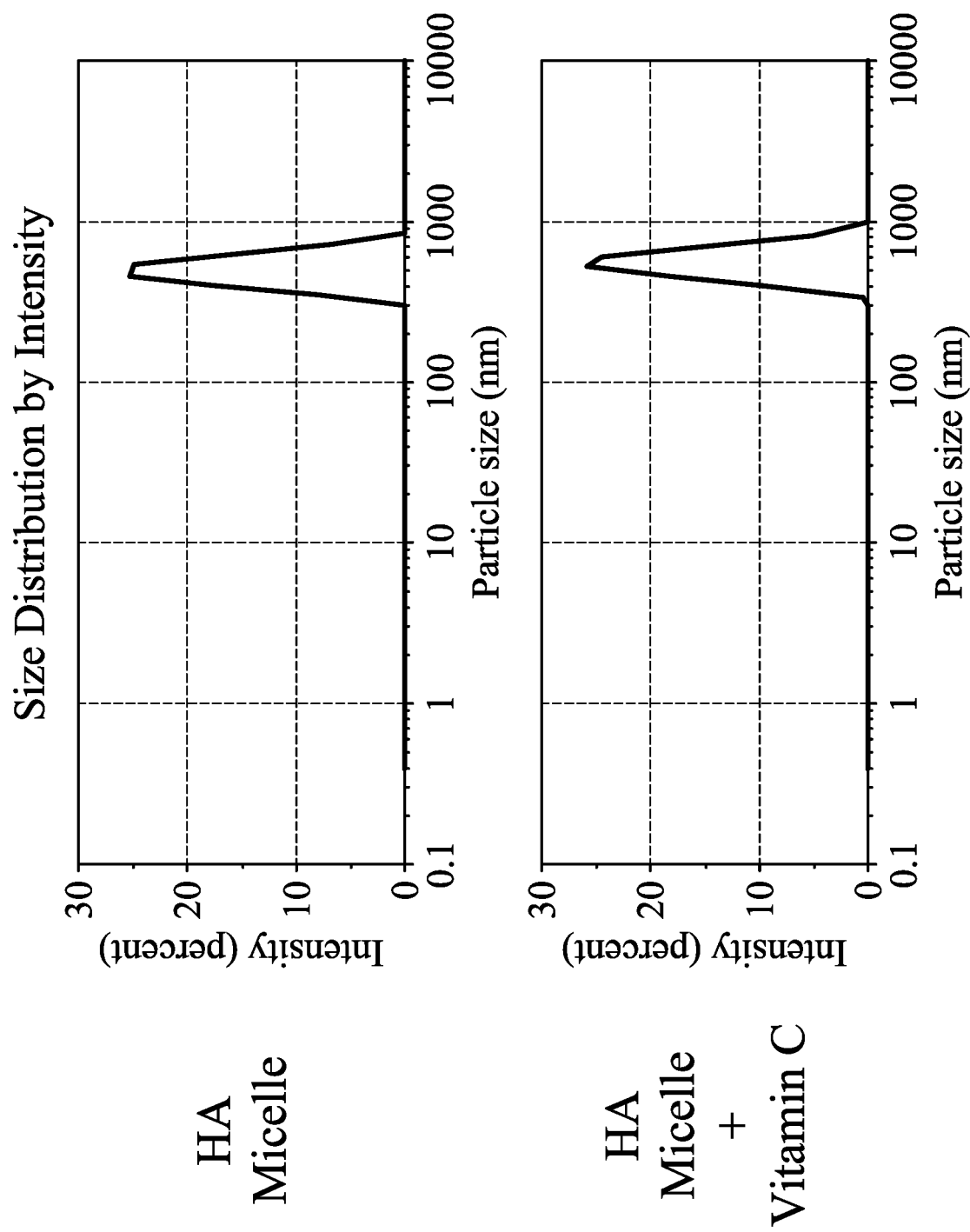
FIG. 4 shows particle size distribution by dynamic light scattering (DLS) of HA micelle before and after coating antioxidant (vitamin C). The upper diagram represents the particle size of the HA micelle that do not coat vitamin C, while the lower diagram represents the particle size of the HA micelles that have coated vitamin C.

According to the upper diagram and the lower diagram of FIG. 4, the HA Micelle particle size before coating vitamin C is 632.4 nm, and the HA Micelle particle size after coating vitamin C (vitamin C: HA Micelle=1:10) is increased to 682.4 nm. In addition, dispersion degrees of HA Micelle before and after coating vitamin C both are good, wherein the dispersion coefficient (PDI) before coating is 0.319 while the dispersion coefficient after coating is 0.378, and the particle size is uniform. It is shown that the particle size of HA Micelle after coating vitamin C will increase, but HA Micelle still maintains good dispersion.

7. Evaluation of Antioxidant Capacity of Antioxidant after being Coated with HA Micelle In order to confirm whether antioxidant such as vitamin C being coated with HA Micelle can improve the antioxidant capacity of the coated antioxidant or not, antioxidant capacity assay is performed on HA Micelle of "6. Preparation of Material 6: Preparation of HA Micelle coated-vitamin C (ascorbic acid)" mentioned above by the method "12. Method 5: ABTS free radical scavenging assay" mentioned above. The results are shown in FIG. 5A and FIG. 5B.

(1) Evaluate of ABTS Free Radical Scavenging Capacity

Figure 5A:
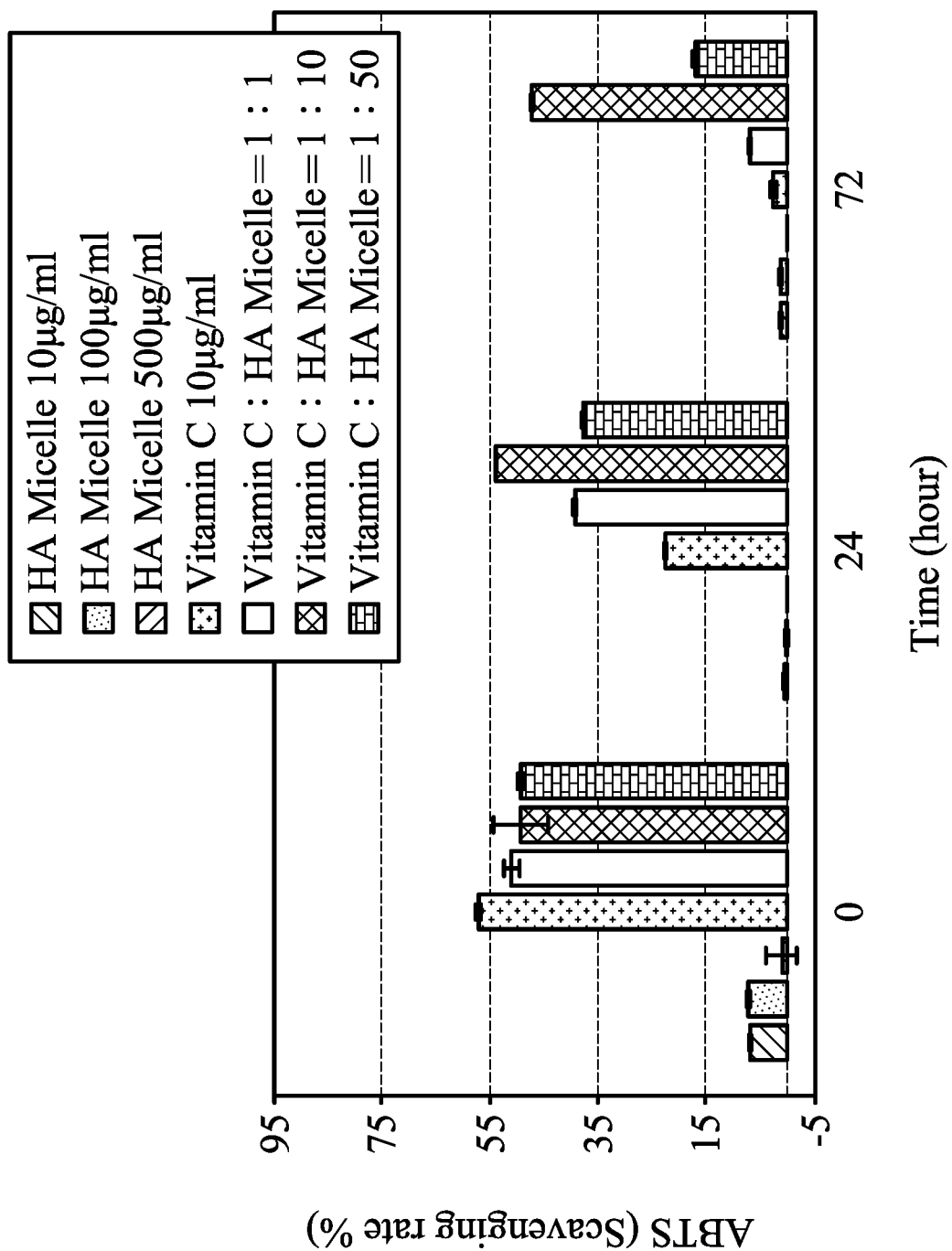
FIG. 5A shows the results of a test for evaluating the antioxidant capacity of HA micelles after coating vitamin C by ABTS free radical scavenging assay.
Figure 5B:
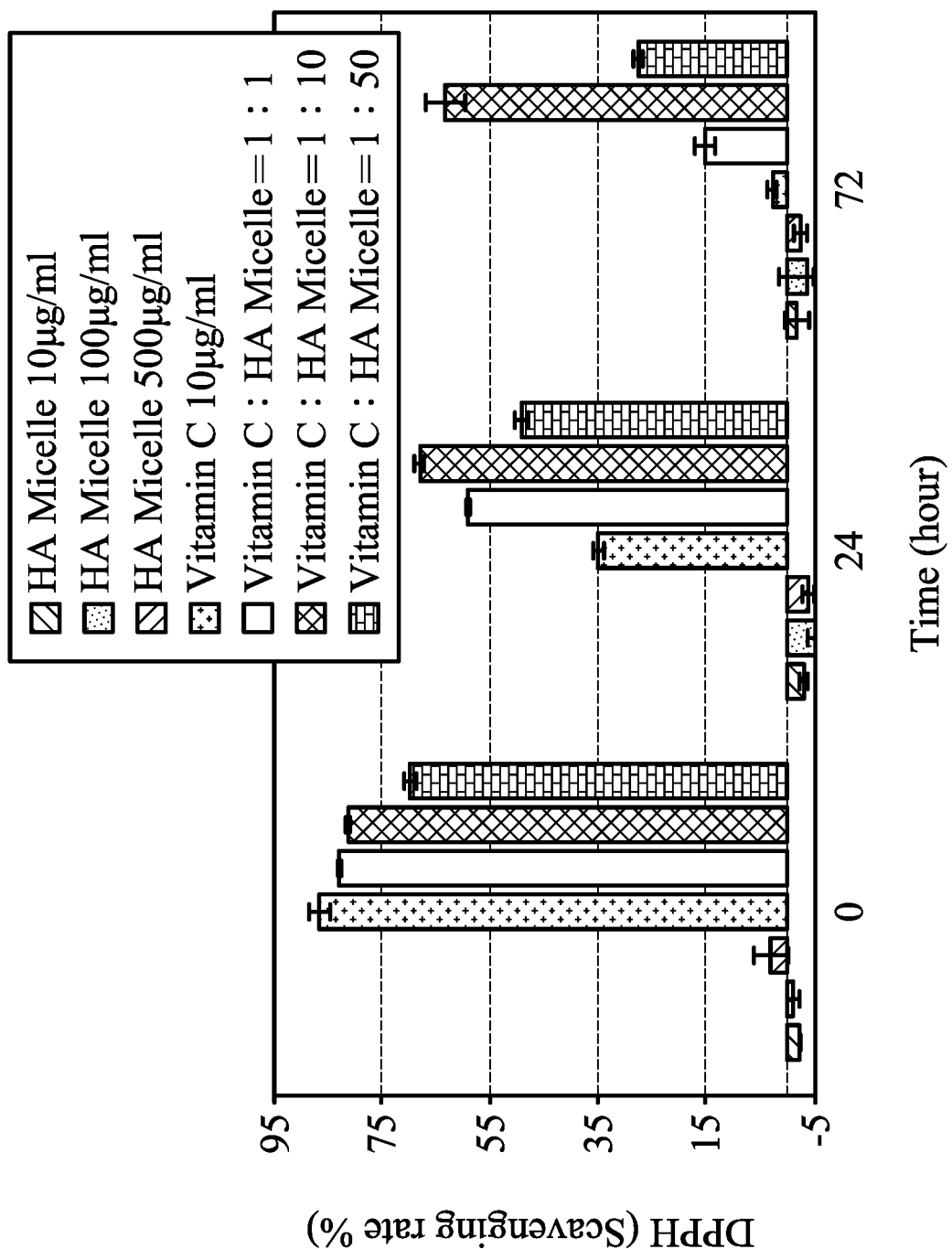
FIG. 5B shows the results of a test for evaluating the antioxidant capacity of HA micelles after coating vitamin C by DPPH free radical scavenging assay.

According to the results of ABTS radical scavenging assay shown in FIG. 5A, simple HA Micelle (10 μg/ml, 100 μg/ml, 500 μg/ml) does not have the ability to scavenge ABTS.' at normal temperature. The ABTS.' radical ion scavenging rate of simple vitamin C 10 μg/ml is 57.08% at 0 hours, and decreases to 22.45% after 24 hours. After 72 hours, only 2.49% of free radical scavenging rate remains, almost losing antioxidant capacity. In contrast, under the coating of HA Micelle, the decline of ABTS.' radical ion scavenging ability of vitamin C is slowed down. The coating ratio of vitamin C:HA Micelle=1:10 has better protection to vitamin C, wherein at the beginning of 0 hours, the ABTS.' radical ion scavenging ability of vitamin C is 56.27%, and after 24 hours, vitamin C almost maintains the same initial scavenging ability, and still has more than 80% (48.34%) of the initial antioxidant capacity in 72 hours. It shows that the coating of HA Micelle has a protective effect on vitamin C and can significantly reduce the degree of decline of antioxidant capacity of vitamin C.

(2) Evaluate of DPPH Free Radical Capture Ability

According to the results of the DPPH radical scavenging assay shown in FIG. 5B, HA Micelle (10 μg/ml, 100 μg/ml, 500 μg/ml) does not have the ability to capture DPPH radicals under normal temperature conditions. The DPPH free radical capture rate of simple vitamin C 10 μg/ml at 0 hour is 86.77%, and the antioxidant capacity decreases by about 60% after 24 hours, that is, the DPPH radical capture rate of decreases to 34.67%. After 72 hours, there is almost no antioxidant capacity, and the DPPH free radical capture rate is only 2.99%. In contrast, under the coating of HA Micelle, the decline of the DPPH radical capture rate of vitamin is slowed down. The coating ratio of vitamin C:HA Micelle=1:10 has better protection to vitamin C, wherein at the beginning of 0 hours, the DPPH free radical capture rate of vitamin C is 80.16%, and more than 70% (60.05%) of the initial antioxidant capacity is maintained until 72 hours. It shows that the coating of HA Micelle has a protective effect on vitamin C, and can significantly reduce the degree of decline of antioxidant capacity of vitamin C. Conversely, without the protection of HA Micelle, the antioxidant capacity of vitamin C will decline rapidly.

Figure 6A:
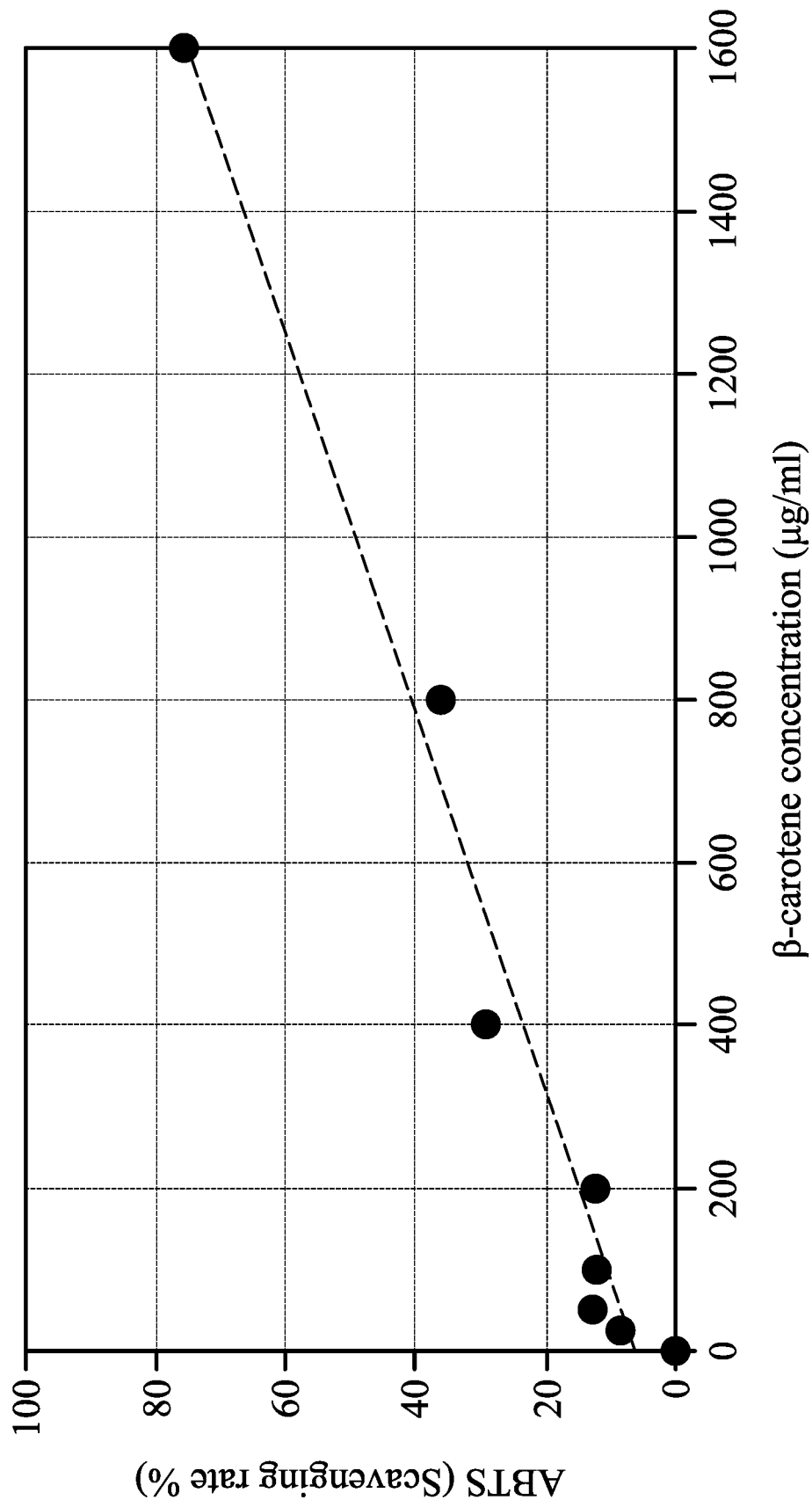
FIG. 6A shows the $IC_{50}$ of HA micelles after coating β-carotene by ABTS free radical scavenging assay.
Figure 6B:
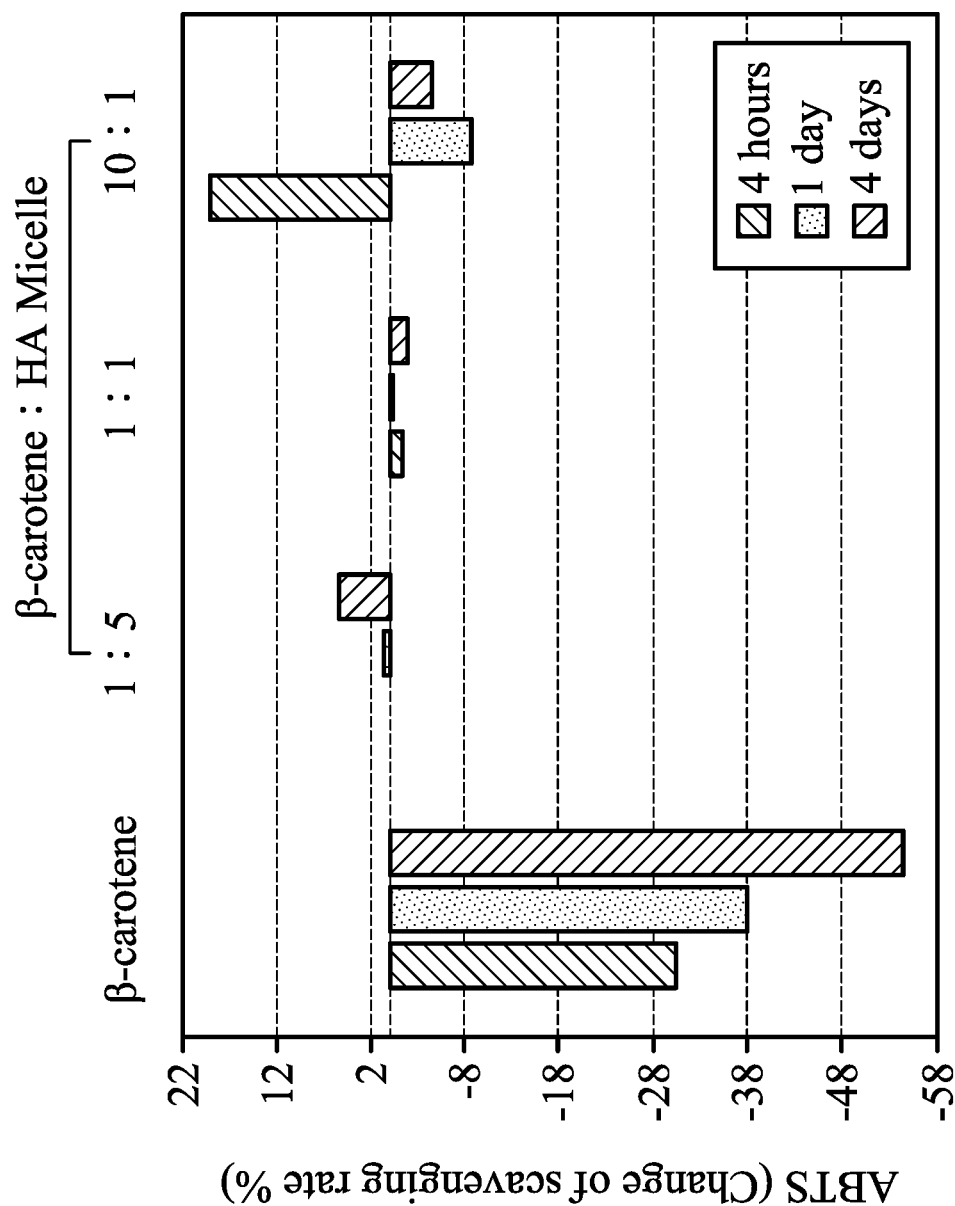
FIG. 6B shows the results of a test for evaluating the antioxidant capacity of HA micelles after coating β-carotene by ABTS free radical scavenging assay.

Evaluation of Antioxidant Capacity of Other Antioxidant after being Coated with HA Micelle In order to confirm whether the coating of HA Micelle does have an effect of increasing antioxidant capacity on other antioxidants other than vitamin C, first, a concentration of β-carotene at which ABTS.' radical ion scavenging rate reaches 50% is estimated, and then antioxidant capacity assay is performed on HA Micelle of "7. Preparation of Material 7: Preparation of HA Micelle coated-β-carotene" mentioned above by the method "12. Method 5: ABTS free radical scavenging assay" mentioned above. The results are shown in FIG. 6A and FIG. 6B.

Assessment with ABTS IC50

β-carotene solutions with concentrations of 1600 µg/ml, 800 µg/ml, 400 µg/ml, 200 µg/ml, 100 µg/ml, 50 µg/ml, and 25 µg/ml were prepared using 50% alcohol as solvent. At the same time, the ABTS.' radical ion scavenging ability of β-carotene solutions at each concentration was detected, and a calibration curve was plotted by the detection results, and a concentration of β-carotene at which ABTS.' radical ion scavenging rate reaches 50% (IC50) was obtained as 1017.5 µg/ml. Subsequently, 800 µg/ml was used as the concentration for (β-carotene at which (β-carotene was coated by HA Micelle.

Evaluate with ABTS Free Radical Scavenging Capacity

According to the results of the ABTS radical scavenging assay shown in FIG. 6A, the simple (β-carotene 800 µg/ml is nearly 30% (30.4%) lower than the initial ABTS.' radical ion scavenging rate within 4 hours at 40° C., and the antioxidant activity after Day 4 was reduce by more than half (54.9%). In contrast, (β-carotene can maintain a certain ABTS.' radical ion scavenging ability under the coating of HA Micelle with different concentrations (800 µg/ml, 4 mg/ml, 8 mg/ml). In particular, the coating ratio of3-carotene:HA Micelle=1:5 has better protection to (β-carotene, and the antioxidant capacity after 4 days can be increased by 5.4%. It is shown that the coating of HA Micelle also has a protective effect on (β-carotene, and can significantly slow down the degree of decline in the antioxidant capacity of carotene.

In summary, in some embodiments, a biomedical composition comprising HA Micelle, or a biomedical composition comprising HA Micelle with at least one antioxidant (such as vitamin C or (β-carotene) is provided. These biomedical compositions at least have the following advantages:

(1) A biomedical composition comprising HA Micelle can increase the secretion amount of growth factors or cytokines (such as PDGF, FGF, GM-CSF) in a region near the wound, and promote matrix reconstruction and tissue reconstruction in a region near the wound to accelerate healing of the wound.

(2) The biomedical composition comprising HA Micelle can significantly promote the proliferation of collagen, thereby improving the problem of collagen loss caused by aging or skin damage.

(3) The essence formulated with HA Micelle not only enhances collagen density, increases skin hydration and water retention, improves skin firmness, but also improves problems of pore and skin roughness. Therefore, it can provide a multi-faceted improvement on the skin texture of the human body.

(4) The biomedical composition in which the antioxidant is coated with HA Micelle can significantly slow down a rate of decomposing an antioxidant, thereby prolonging the effectiveness of the antioxidant. Moreover, even at high temperatures, HA Micelle can protect the coated antioxidants and significantly slow down the decomposition rate of antioxidants.

(5) The biomedical composition in which the antioxidant is coated with HA Micelle can significantly slow down the degree of decline in the antioxidant capacity of the antioxidant, thereby stabilizing the antioxidant and prolonging its activity, and greatly improving a situation in which the antioxidant capacity of the antioxidant rapidly decline.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for skin care and/or maintenance, comprising:
    applying or administering a preparation for skin care and/or maintenance to the skin of a subject in need thereof, wherein the preparation comprises a biomedical composition, and wherein the biomedical composition comprises:
    an effective amount of micelle, wherein the micelle comprises:
    a hyaluronic acid and/or a derivative thereof; and
    a modified histidine, wherein the modified histidine is grafted to at least one primary hydroxyl group of the hyaluronic acid and/or the derivative thereof, and a graft ratio of the modified histidine is 1-100%,
    wherein the modified histidine is at least one selected from the group consisting of Boc-histidine, Cbz-histidine, Fmoc-histidine and Ac-histidine, and the hyaluronic acid and/or the derivative thereof and the modified histidine form the micelle on a weight percentage of 0.2-300:1.

2. The method for skin care and/or maintenance as claimed in claim 1, wherein a molecular weight of the hyaluronic acid and/or the derivative thereof is 7,000-1,500,000.

3. The method for skin care and/or maintenance as claimed in claim 1, wherein a weight percentage of the effective amount of micelle is 0.001 wt %-1 wt %.

4. The method for skin care and/or maintenance as claimed in claim 1, wherein a modification technique for hyaluronic acid derivative is at least one selected from a group consisting of crosslinking a hyaluronic acid with adipic acid dihydrazide (ADH), crosslinking a hyaluronic acid with 1,4-butanediol diglycidyl ether (BDDE), crosslinking a hyaluronic acid with 1-ethyl-3-(3-dimethylaminopropyl)carbodiimide (EDC), crosslinking a hyaluronic acid with divinyl sulphone (DVS) crosslinking a hyaluronic acid with glycidyl methacrylate (GMA), modifying a hyaluronic acid with polylactic acid (PLA), modifying a hyaluronic acid with 4-vinylbenzyl chloride (VBC) and modifying a hyaluronic acid with cetyltrimethylammonium bromide (CTAB).

5. The method for skin care and/or maintenance as claimed in claim 1, wherein the preparation is an emulsion or a dispersion.

6. A method for promoting collagen proliferation, growth factor secretion, and/or cytokine secretion, comprising:
    applying or administering a preparation for promoting collagen proliferation, growth factor secretion, and/or cytokine secretion to the skin of a subject in need thereof, wherein the preparation comprises a biomedical composition, and wherein the biomedical composition comprises:
an effective amount of micelle, wherein the micelle comprises:
a hyaluronic acid and/or a derivative thereof; and
a modified histidine, wherein the modified histidine is grafted to at least one primary hydroxyl group of the hyaluronic acid and/or the derivative thereof, and the graft ratio of the modified histidine is 1-100%,
wherein the modified histidine is at least one selected from the group consisting of Boc-histidine, Cbz-histidine, Fmoc-histidine and Ac-histidine, and the hyaluronic acid and/or the derivative thereof and the modified histidine form the micelle on a weight percentage of 0.2-300:1.

7. The method for promoting collagen proliferation, growth factor secretion, and/or cytokine secretion as claimed in claim 6, wherein a molecular weight of the hyaluronic acid and/or the derivative thereof is 7,000-1,500,000.

8. The method for promoting collagen proliferation, growth factor secretion, and/or cytokine secretion as claimed in claim 6, wherein a weight percentage of the effective amount of micelle is 0.001 wt %-1 wt %.

9. The method for promoting collagen proliferation, growth factor secretion, and/or cytokine secretion as claimed in claim 6, wherein a modification technique for hyaluronic acid derivative is at least one selected from a group consisting of crosslinking a hyaluronic acid with adipic acid dihydrazide (ADH), crosslinking a hyaluronic acid with 1,4-butanediol diglycidyl ether (BDDE), crosslinking a hyaluronic acid with 1-ethyl-3-(3-dimethylaminopropyl)carbodiimide (EDC), crosslinking a hyaluronic acid with divinyl sulphone (DVS) crosslinking a hyaluronic acid with glycidyl methacrylate (GMA), modifying a hyaluronic acid with polylactic acid (PLA), modifying a hyaluronic acid with 4-vinylbenzyl chloride (VBC) and modifying a hyaluronic acid with cetyltrimethylammonium bromide (CTAB).

10. The method for promoting collagen proliferation, growth factor secretion, and/or cytokine secretion as claimed in claim 6, wherein the preparation is an emulsion or a dispersion.

11. The method for promoting collagen proliferation, growth factor secretion, and/or cytokine secretion as claimed in claim 6, wherein the growth factor and/or the cytokine comprises PDGF, FGF, GM-CSF, IL-1 or IL-8.

12. The method for promoting collagen proliferation, growth factor secretion, and/or cytokine secretion as claimed in claim 6, wherein an administering technique for the biomedical composition comprises oral administration, parenteral administration, inhalation spray or implanted reservoir.

13. The method for promoting collagen proliferation, growth factor secretion, and/or cytokine secretion as claimed in claim 6, wherein the parenteral administration comprises dressing, subcutaneous injection or intravenous injection.

14. A biomedical composition, comprising:
a hyaluronic acid and/or a derivative thereof;
a modified histidine, wherein the modified histidine is grafted to at least one primary hydroxyl group of the hyaluronic acid and/or the derivative thereof, and the graft ratio of the modified histidine is 1-100%; and
at least one antioxidant,
wherein the modified histidine is at least one selected from the group consisting of Boc-histidine, Cbz-histidine, Fmoc-histidine and Ac-histidine; the hyaluronic acid and/or the derivative thereof and the modified histidine form an effective amount of micelle on a weight percentage of 0.2-300:1; the at least one antioxidant is coated with the micelle; and a weight ratio of the effective amount of micelle to the at least one antioxidant is 0.1-500.

15. The biomedical composition as claimed in claim 14, wherein a modification technique for hyaluronic acid derivative is at least one selected from a group consisting of crosslinking a hyaluronic acid with adipic acid dihydrazide (ADH), crosslinking a hyaluronic acid with 1,4-butanediol diglycidyl ether (BDDE), crosslinking a hyaluronic acid with 1-ethyl-3-(3-dimethylaminopropyl)carbodiimide (EDC), crosslinking a hyaluronic acid with divinyl sulphone (DVS) crosslinking a hyaluronic acid with glycidyl methacrylate (GMA), modifying a hyaluronic acid with polylactic acid (PLA), modifying a hyaluronic acid with 4-vinylbenzyl chloride (VBC) and modifying a hyaluronic acid with cetyltrimethylammonium bromide (CTAB).

16. The biomedical composition as claimed in claim 14, wherein the at least one antioxidant is at least one selected from a group consisting of proanthocyanidins, glutathione (GSH), lipoic acid, astaxanthin, Vitamin E, β-carotene, coenzyme Q and isoflavones.

17. The biomedical composition as claimed in claim 14, further comprising a pharmaceutically acceptable carrier or salt.

* * * * *